(12) United States Patent
Roschak et al.

(10) Patent No.: US 8,323,202 B2
(45) Date of Patent: Dec. 4, 2012

(54) METHOD AND SYSTEM FOR MEASURING PULMONARY ARTERY CIRCULATION INFORMATION

(75) Inventors: Edmund J. Roschak, Mission Viejo, CA (US); Jeffrey Schwardt, Palo Alto, CA (US); Philip Stephen Levin, Storrs, CT (US)

(73) Assignee: PneumRx, Inc., Mountain View, CA (US)

( * ) Notice: Subject to any disclaimer, the term of this patent is extended or adjusted under 35 U.S.C. 154(b) by 788 days.

(21) Appl. No.: 12/272,703

(22) Filed: Nov. 17, 2008

(65) Prior Publication Data

US 2009/0131765 A1    May 21, 2009

Related U.S. Application Data

(60) Provisional application No. 60/988,738, filed on Nov. 16, 2007.

(51) Int. Cl.
   *A61B 8/14*  (2006.01)
(52) U.S. Cl. ........ 600/465; 600/301; 600/453; 600/454; 600/462
(58) Field of Classification Search .................. 600/301, 600/453, 437, 454, 462, 465
   See application file for complete search history.

(56) References Cited

U.S. PATENT DOCUMENTS

| | | | |
|---|---|---|---|
| 4,103,679 A | 8/1978 | Aronson | |
| 4,327,739 A | 5/1982 | Chmiel et al. | |
| 4,856,529 A | 8/1989 | Segal | |
| 5,078,148 A | 1/1992 | Nassi et al. | |
| 5,339,816 A | 8/1994 | Akamatsu et al. | |
| 5,623,930 A | 4/1997 | Wright et al. | |
| 6,024,704 A | 2/2000 | Meador et al. | |
| 6,368,283 B1 | 4/2002 | Xu et al. | |
| 6,719,698 B2 * | 4/2004 | Manor et al. | 600/454 |
| 6,961,600 B2 * | 11/2005 | Kohl et al. | 600/339 |
| 7,022,088 B2 | 4/2006 | Keast et al. | |
| 7,963,925 B1 * | 6/2011 | Schecter | 600/508 |
| 2001/0039383 A1 | 11/2001 | Mohler | |
| 2007/0016072 A1 * | 1/2007 | Grunwald et al. | 600/468 |
| 2008/0312543 A1 | 12/2008 | Laufer et al. | |
| 2009/0318904 A9 | 12/2009 | Cooper et al. | |

OTHER PUBLICATIONS

Kitabatake et al. "Non-Invasive Evaluation of Pulmonary Hypertension by a Pulsed Doppler Technique". Circulation 68: 302-309 (1983).

* cited by examiner

*Primary Examiner* — Brian Casler
*Assistant Examiner* — Daniel Huntley
(74) *Attorney, Agent, or Firm* — Kilpatrick Townsend and Stockton LLP

(57) ABSTRACT

Minimally invasive systems and methods are described for measuring pulmonary circulation information from the pulmonary arteries. A transbronchial Doppler ultrasound catheter is advanced through the airways and in the vicinity of the pulmonary artery. Doppler ultrasound energy is sent through the airway wall and across the pulmonary artery to obtain velocity information of blood flowing through the artery. The velocity information is used to compute pulmonary circulation information including but not limited to flowrate.

22 Claims, 7 Drawing Sheets

METHOD AND SYSTEM FOR MEASURING PULMONARY ARTERY CIRCULATION INFORMATION

CROSS-REFERENCE TO RELATED APPLICATIONS

This application claims priority to U.S. Patent Application No. 60/988,738, filed Nov. 16, 2007 the entirety of which is incorporated by reference.

BACKGROUND OF THE INVENTION

It is well established that assessing pulmonary arterial pressure (PAP) is useful in diagnosing pulmonary disease such as pulmonary hypertension. PAP, however, may remain relatively unchanged following clinical treatment to address pulmonary hypertension. Thus, while useful as an indicator of the presence of pulmonary disease, PAP alone may not be practical for evaluating improvement and patient response to treatment. For this reason, additional pulmonary circulation information is desired.

Total pulmonary vascular resistance (TPR) provides information about the flowrate and pressure in the pulmonary vasculature. TPR is a ratio of the PAP to flowrate. Unlike PAP, TPR changes to some degree in response to treatment and can therefore be used to help assess the efficacy or degree of the treatment effect that eventually results in patient improvement.

Various approaches are available to obtain pulmonary information. For example, a passive approach is disclosed in Patent Pub. No. 2001/0039383 to Mohler. In this application, a sensor assembly is provided that detects heart sounds. The sensor is placed in contact with the skin, and is connected with a signal processing means. Pressure information is measured based on acoustic wave signatures arising from the heart. See also U.S. Pat. No. 6,368,283 to Xu et al.

A more invasive approach involves implanting a medical device for sensing the absolute and barometric pressures as disclosed in U.S. Pat. No. 6,024,704 to Meador et al. The implantable sensor described in Meador includes two leads. One lead is positioned in the subcutaneous layer of the skin for measuring the barometric pressure and a second lead is positioned in the right ventricle of the heart for measuring pressure therein. The contents of the above teachings are incorporated by reference in their entirety and may be optionally combined with the methods and devices described herein.

Despite the results of the above mentioned measurement techniques, an invasive catheterization procedure is still considered by many physicians to be the gold standard to confirm pulmonary hypertension and for determining the PAP. In a right heart catheterization, a catheter is inserted through the pulmonary arteries and into the right ventricle of the heart. Once positioned in the right ventricle, the pulmonary pressure is measured directly using a pressure sensor. However, this procedure requires penetration of the vasculature, and requires significant surgical intervention. As such, the procedure carries an undesirable amount of inconvenience, cost, and risk to the patient.

A more convenient, less invasive approach is desired for obtaining accurate pulmonary circulation information.

SUMMARY OF THE INVENTION

Minimally invasive systems and methods are described for measuring pulmonary circulation information from the pulmonary arteries.

Variations of the medical systems for measuring pulmonary circulation information of the pulmonary artery include a catheter comprising at least one ultrasonic transducer, and an ultrasound Doppler signal processing unit for processing signals sent by and received from the transducer. The system can also include a processor or processor means for analyzing the Doppler signals to perform the analysis of the pulmonary circulation information disclosed herein. In such a case, the processor or processor means can include a typical microprocessor based device that is either discrete from or integral with the Doppler signal processing unit. The system can also include a visual indicator. The visual indicator can be located on either the face of the control unit or the processor. Alternatively, or in combination, the visual indicator can transmit signals to another monitor (such as those used with a bronchoscope) so that information can be displayed on the monitor and observed by the physician during the procedure.

In one variation, the system includes catheters having designs suited for obtaining anatomic information or arterial flow related information. For example, a number of transducers may be located at various angles with respect to an axis of the catheter. In another variation, the transducer(s) can rotate or move within the catheter.

The system can also include a data set of predetermined waveforms obtained by and associated with direct measurement of pulmonary arterial pressure. The data set is used to compare a real-time or other measured pressure signature to one or more of the predetermined waveforms to determine an estimated mean arterial pressure or other pulmonary circulation information. This predetermined data set can be stored within memory means that is integrated with the controller or processor. Alternatively, the data set can be provided to the system via a removable means of data storage. Examples of such memory means are commonly known.

The present invention also includes methods for determining pulmonary circulation information in a pulmonary artery without puncturing or opening the pulmonary artery. The methods include providing an ultrasound Doppler catheter, said catheter comprising a distal section and at least one ultrasound transducer in said distal section, advancing said distal section of said ultrasound Doppler catheter through a natural respiratory opening, and into an airway and to a location along an airway wall such that at least a portion of said distal section and said at least one ultrasound transducer is in proximity of the pulmonary artery, sending and receiving ultrasonic waves to said pulmonary artery from said ultrasound transducer; determining a measured pressure signature by analyzing the received ultrasonic waves, and comparing the measured pressure signature to one or more predetermined pressure signatures wherein each of said predetermined pressure signatures has an associated mean pulmonary arterial pressure.

The present invention also includes a method for determining flowrate in a blood vessel comprising determining velocity profiles across the blood vessel and computing the flowrate based on said velocity profiles.

The description, objects and advantages of the present invention will become apparent from the detailed description to follow, together with the accompanying drawings. The invention includes any number of combination of method and devices, or aspects of such methods and devices where such combinations are possible.

The disclosure and invention specifically include combination of features of various embodiments as well as combinations of the various embodiments where possible.

BRIEF DESCRIPTION OF THE DRAWINGS

FIG. 9b is a plot of a velocity profile across the tissue region illustrated in FIG. 9a.

DETAILED DESCRIPTION OF THE INVENTION

Novel systems and methods to determine pulmonary circulation information are described herein. In particular, the systems and method can include minimally invasive approaches to determine pulmonary circulation information. In one variation, a transbronchial or bronchoscopic approach is described that measures pulmonary pressure and volumetric flowrate of the fluid in the pulmonary artery. The described system is capable of measuring various indicia of pulmonary circulation information without the need or requirement to penetrate the arterial wall or otherwise enter the vasculature. In additional variations, the systems described herein can be combined with conventional measurement modes for improved assessment of pulmonary circulation.

Figure 1:
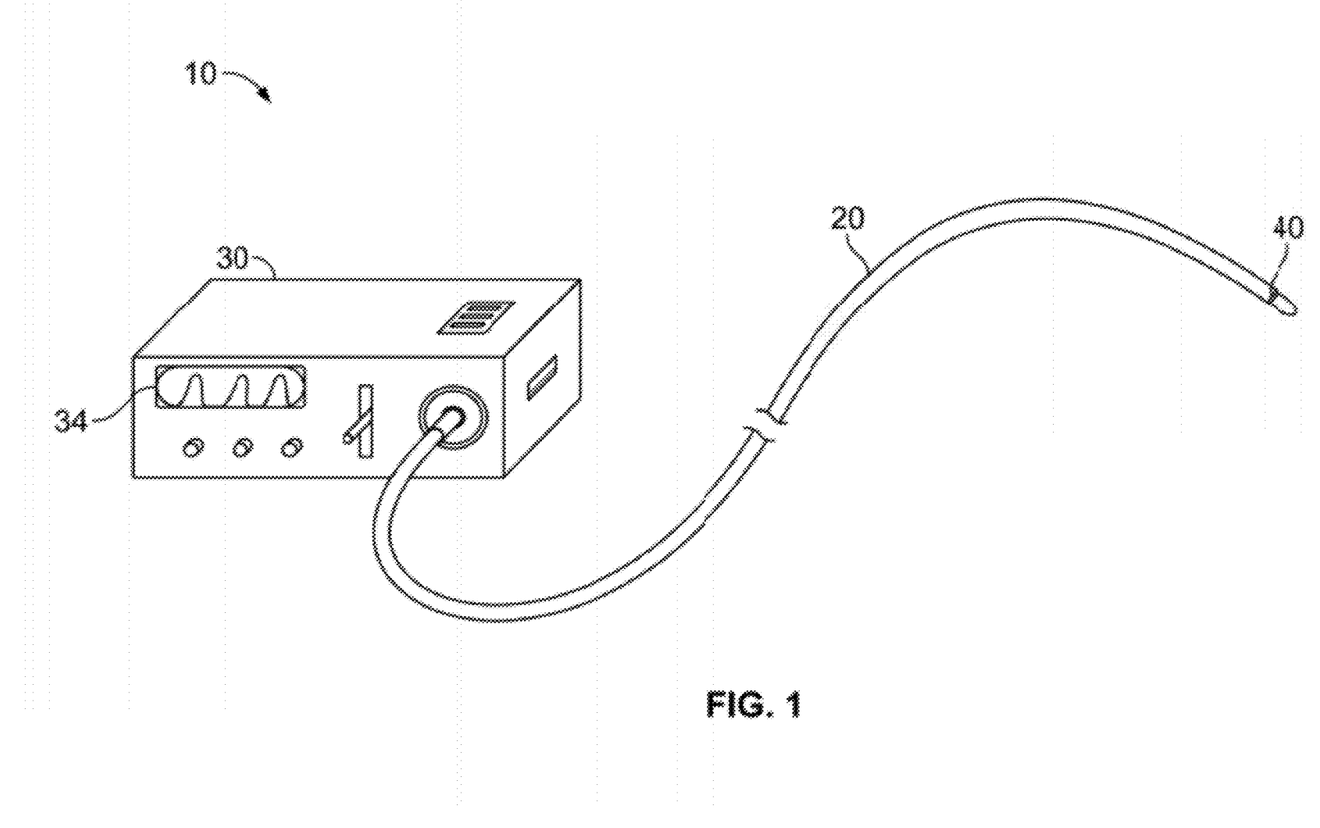
FIG. 1 is an illustration of a catheter system in accordance with the present invention.

FIG. 1 illustrates a catheter system in accordance with one embodiment of the present invention. System 10 includes a Doppler ultrasound catheter 20 and a signal processing unit 30. The processing unit 30 can also include a processor or processor means for analyzing the Doppler signals to perform the analysis of the pulmonary circulation information disclosed herein. Alternatively, the processor means may be a separate component. However, such a processor can be incorporated together with the Doppler processing unit 30.

FIG. 1 also illustrates the processing unit 30 as including a visual indicator 34 or display. In additional variations, the visual indicator 34 can comprise a signal generated by the system that causes visual information or other data to be displayed on a monitor coupled to the bronchoscope.

The catheter 20 includes a flexible shaft and a distal working end section. The distal section comprises an ultrasound transducer 40 that is electrically coupled to the signal processing unit (SPU) 30. As will be discussed further below, Doppler ultrasound analysis is carried out to identify and determine various attributes of the pulmonary blood flow such as flowrate and pressure. However, other non-invasive imaging or measurement modalities can be used with the principles of the invention such as, for example, laser Doppler.

Figure 2:
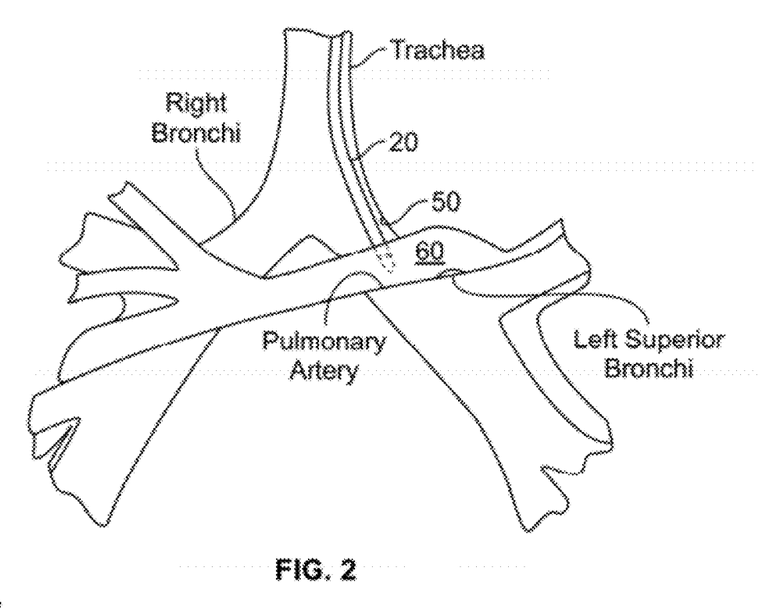
FIG. 2 is an anterior view of a catheter positioned in the bronchi and in the vicinity of a pulmonary artery.

One application of the above mentioned system is shown in FIG. 2. In particular, the ultrasound catheter 20 extends through the trachea and into the left bronchi 50. The end of the catheter is shown behind or posterior to the pulmonary artery 60. As shown, the catheter can extend independently in the airways. However, the present invention may be carried out with the use of a bronchoscope or other guiding sheath, where the catheter may be extended through the bronchoscope or guiding sheath. A bronchoscope provides an additional mechanism to view the procedure.

Figure 3:
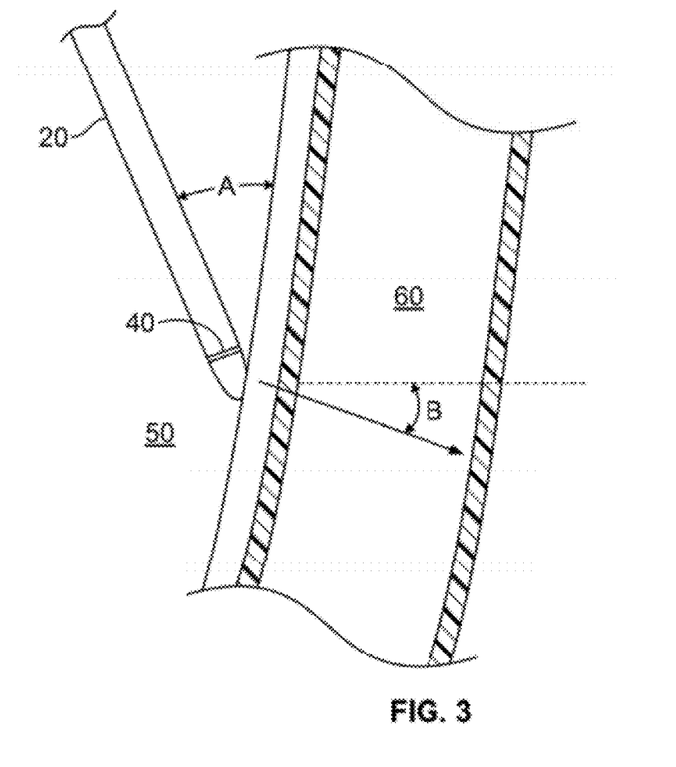
FIG. 3 is an enlarged view of a catheter distal end in accordance with one embodiment of the present invention.

FIG. 3 illustrates the distal end section of catheter 20 within bronchi 50 and in the vicinity of the pulmonary artery 60. The tip is shown in contact with the airway wall. Once positioned at a location along the airway, and in the vicinity of the pulmonary artery 60, various circulation information of the pulmonary artery may be determined such as, but not limited to: the arterial pressure, blood-flow velocity, arterial diameter and cross-sectional area, blood flowrate, cardiac output, and total pulmonary resistance (TPR). The entire blood-flow velocity waveform in response to right ventricle contraction and filling may also be collected.

Pulmonary Arterial Pressure

Pulmonary arterial pressure (PAP) may be determined by various techniques including without limitation ultrasound waveform analysis. Ultrasound waveform analysis is carried out by sending and receiving ultrasound waves from the ultrasonic transducer 40 and relies on a Doppler Effect measurement to obtain flow-rate waveforms. The measurements may occur over a duration of time or over a number of heart beats. The actual waveform characteristics are then compared to known (or predetermined) waveform information. For example, the waveform characteristics of healthy and diseased individuals can be established as baselines. In practice, the measured flow pattern is then compared to the base waveforms of healthy and diseased patients to assess whether a flow pattern indicates pulmonary hypertension.

Method of non-invasively determining pulmonary hypertension by Doppler or other means are discussed in Non-Invasive Evaluation of Pulmonary Hypertension by a Pulsed Doppler technique by A. Kitabatake (Circulation 1983; 68; 302-309). However, these techniques require visualization from outside the body. Moreover, such external imaging of COPD patients is difficult in view of the large amount of air trapped within hyper-inflated lungs. More direct measuring of characteristics of blood pressure and assessing pulmonary hypertension from within an airway under the present invention overcomes these problems. For COPD patients, the method of the present invention may be used to capture waveforms that might be unobtainable using the transthoracic technique described by Kitabatake As noted above, the precursor (or actual, or measured) pressure signature is compared to a set of predetermined (or baseline) waveforms, each of which corresponds to a specific mPAP. The database is preferably created by comparing characteristics of collected waveforms to pressure measurements obtained by a traditional standard such as the right heart catheterization. Preferably, the database includes a range of predetermined waveforms correlated to mean pulmonary pressures from 10 to 80 mmHg, with standard of deviation of 5. If the physician determines treatment is necessary, the physician can administer the appropriate treatment (e.g., surgical intervention, drugs, etc.). The physician can then assess the effects of such treatment by obtaining an additional pressure or waveform signatures.

A waveform analysis process is further described in commonly assigned Provisional application No. 60/944,730, filed Jun. 18, 2007, and entitled MEASUREMENT OF PULMONARY HYPERTENSION FROM WITHIN THE AIRWAYS, the entirety of which is incorporated by reference.

As indicated above, total pulmonary vascular resistance (TPR) is another useful calculation for the physician. TPR is a ratio of the pulmonary artery pressure to the cardiac output, namely, volumetric flowrate (Q). Hence, the flowrate must be determined in order to determine TPR.

Pulmonary Arterial Flowrate

Flowrate may be determined using a number of different approaches. A first approach obtains flowrate (Q) by determining the velocity, and the cross sectional area, and multiplying the two numbers according to the equation $Q=V \times A$, where $A$ is cross sectional area and $V$ is average velocity within that cross sectional area.

Velocity (V) may be calculated using Doppler shifting analysis with the Doppler catheter system described above. A series of ultrasound waves are delivered from transducer 40, reflected off moving objects (namely, blood cells, microbubbles, or the like) in the fluid. These reflected waves or signals are sampled at a series of intervals corresponding to round trip transit times between the transducer 40 and the various sample volumes within the blood vessel. The blood flow velocity of each sample volume can then be determined by detecting the Doppler frequency shift of the transmitted signal using well known techniques.

The direction of blood flow can be determined using two reference ultrasound signals that are generated at 90 degrees out of phase with each other. Utilizing such techniques it is possible to map a one dimensional velocity profile by establishing a number of individual range gates and spanning the diameter of the blood vessel in which the transducer is positioned. There are a number of intravascular examples of this type of measurement such as that described in U.S. Pat. Nos. 5,339,816 and 4,856,529 (each of which is incorporated by reference).

The cross-sectional area (A) is proportional to the square of the diameter of the vessel. In particular, $A=\pi \times D^2/4$. Consequently, in this embodiment of the invention, the diameter (D) or radius is measured or estimated in order to determine A.

The vessel diameter (D) can be determined utilizing automatic diameter detection system of the type well known to those skilled in the art. For example, U.S. Pat. No. 4,856,529 describes a system which provides dynamic range-gating and diameter detection utilizing Doppler shifted ultrasonic power within three sample gates. The gates correspond to one centered on the distal vessel wall, one near the vessel wall and one within the center of the vessel. A feedback loop adjusts gate positions so that reflected Doppler power from the far wall is a preset fraction of the Doppler power obtained from a sample volume located entirely within the central vessel lumen. The vessel diameter is then determined by continuously detecting the delay transit time to the far sample gate as it is adjusted to remain centered on the far wall. Instantaneous flow is calculated from the instantaneous space average velocity and instantaneous diameter using formulas well known to those skilled in the art.

Another technique for measuring the diameter is based on a time of flight analysis and is described in, for example, U.S. Pat. No. 5,078,148 to Nassi et al. Still other techniques may be employed to measure the diameter and cross-sectional area of the blood vessel and the invention is intended only to be limited to the appended claims.

One complexity in analyzing the Doppler time of flight data is compensating for the angle of the ultrasound waves relative to the vessel wall or fluid flow. In particular, with reference to FIG. 3, the direction of propagation of the ultrasound waves may be at an angle (B) to the diameter (D). In the event the ultrasound pulses and waves propagate through the fluid at an angle (B), the diameter may be estimated larger than its actual value. It is therefore useful to estimate or identify the angle (B) and compensate for an increase or decrease in measured distances.

One technique for estimating the angle (B) is illustrated in FIG. 3. The catheter 20 comprises a single transducer 40. The distal section and transducer 40 may be extended out of a bronchoscope and articulated against the airway wall at a particular angle such as 0, 45, or 90 degrees. In this manner, the angle is ascertained. This angle may be used in combination with the Doppler ultrasound shifting and time of flight information to identify D, A, and V. Alternatively, the catheter distal end may include a mechanical feature or characteristic that repeatably orients the catheter tip at a known angle to blood flow. For example, a pre-existing bend in the distal section can necessarily form a certain angle (A) with the vessel wall. Additionally, a corkscrew shaped distal end, or S-bend shape may reliably locate the transducer in a predictable location and orientation within the airway 50 lumen.

Figure 4:
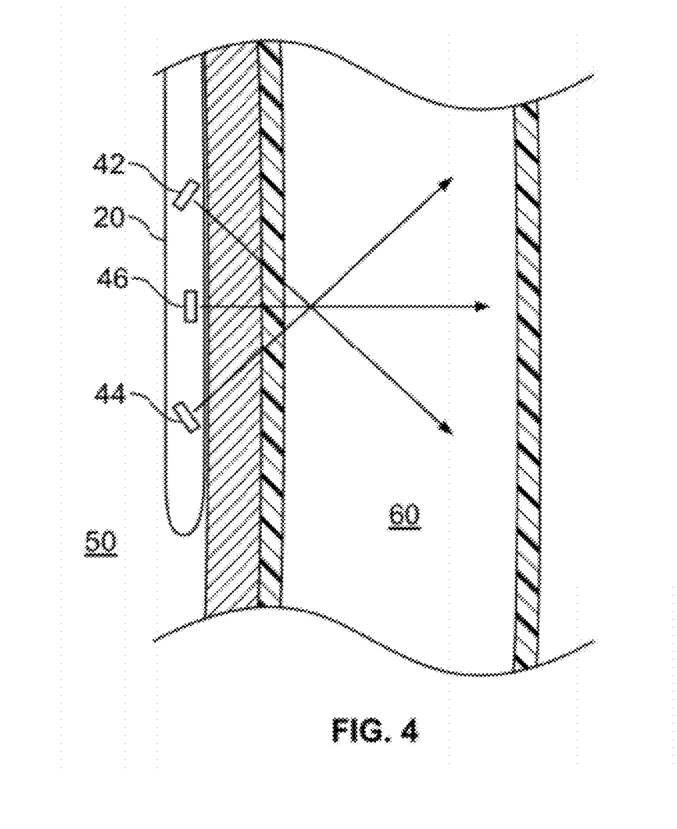
FIG. 4 is an enlarged view of a catheter distal end comprising a plurality of ultrasonic transducers.

Another embodiment is shown in FIG. 4. In the embodiment in FIG. 4, catheter 20 includes a plurality of transducers 42, 44, and 46, each at a fixed angle. Because the angles of the transducers are known, the time of flight ultrasound data can be adjusted to compensate for the angle of the pulmonary artery (or other blood vessel) 60 or catheter. Alternatively, the two or more transducers of FIG. 4 may be utilized to capture Doppler shifted data at more than one angle of incidence to the blood flow. The absolute blood velocity may then be calculated by mathematically eliminating the variable of angle of incidence, as is well known in the art and described, for example, in U.S. Pat. No. 5,339,816.

Figure 5:
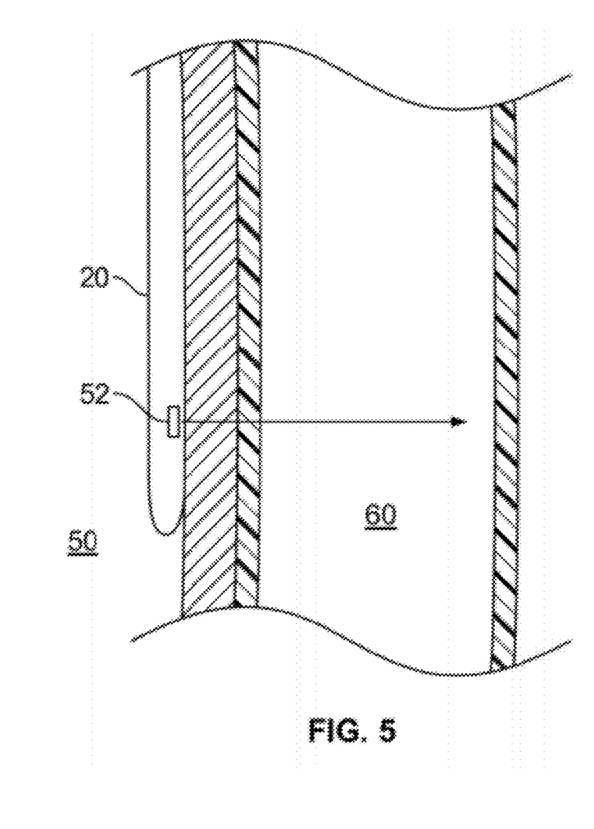
FIG. 5 is an enlarged view of a catheter distal end comprising another embodiment of the present invention.

Another embodiment is shown in FIG. 5. In the embodiment in FIG. 5, catheter 20 is placed flush against the airway wall. Because the transducer is fixed relative to the catheter, the primary direction of propagation of the ultrasound waves is known. As shown, a single transducer 52 sends signals laterally from the distal section. The signals are perpendicular to the direction of fluid flow. Hence, the direction of the ultrasound waves are in the same direction as the diameter D.

Clearly, any of the above systems can also employ various sensing mechanisms to ensure proper contact of the catheter against an airway wall (e.g., establishing an electrical circuit, temperature measurement, ultrasound measurement, etc.)

Another embodiment, not shown, includes a single transducer in the distal section of the catheter. The catheter end section, or transducer itself, is rotated or moved. Information at each location and angle is recorded. A comparison of the sensed information identifies a range of potential dimensions of the diameter. An estimate may then be made in view of the range. For example, the mean may be taken as the closest value to the actual diameter. Or, a weighted average may be made. An example of a rotation technique is described in U.S. Pat. No. 5,623,930.

Another approach for determining flowrate (Q) includes evaluating velocity profiles over time and across a vessel. Notably, it has been found that flowrate may be obtained without directly measuring the cross-sectional area of the vessel. This novel technique is described below.

One embodiment includes providing a pulsed wave ultrasound Doppler probe and pulsed-wave ultrasound Doppler processing unit (e.g. UVP Duo, manufactured by Met-Flow, Laussane, Switzerland). The Doppler probe includes at least one ultrasound transducer. The Doppler probe is advanced through an endoscope or bronchoscope towards an intrabronchial site in either the right or left main bronchus, preferably at a position 0-20 mm distal to the carina. The ultrasound transducer is positioned such that its beam is directed at an angle other than perpendicular to the axis of the vessel (a beam directed exactly 90 degrees would fail to detect a Doppler shift). The beam width is preferably less than the blood vessel diameter.

Figure 6:
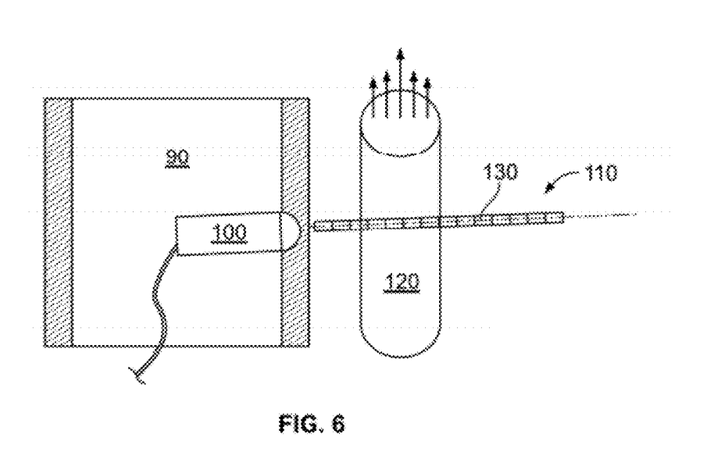
FIG. 6 is an illustration of an ultrasound Doppler probe positioned within an airway and sending a beam through the airway wall and across a blood vessel.

Referring to FIG. 6, a pulsed wave ultrasound Doppler probe 100 involves sending an ultrasound beam 110 across a blood vessel 120. Analysis of reflected ultrasound energy is performed by a signal processor (not shown) of sample volumes 130 positioned sequentially along the path of the ultrasound beam. Preferably at least two, and more preferably at least 3 sampling volumes ought to be positioned along the blood vessel diameter. Stated another way, the length of the sampling volume is preferably less than ½ of the vessel diameter. Non-limiting examples of sample volume length range from about 1 to 3 mm, or less.

In this embodiment, the sampling range (i.e. the distance over which the sampling volumes extend along the beam axis) is greater than the blood vessel diameter, and includes sampling volumes outside the blood vessel. Preferably, the range of sample volumes extends beyond both sides of the blood vessel—from the near or proximal side of the blood vessel, and to the far or distal side of the blood vessel relative to the Doppler transducer. In certain cases in which the flow profile is symmetrical about the vessel axis this method may also be utilized successfully where the range extends from some position within the blood vessel that is proximal to the center of the blood vessel to some position outside the blood vessel, distally. Similarly, the method can be utilized successfully where the range extends from some position proximal to the blood vessel to some position within the blood vessel that is distal to the center of the blood vessel. A non-limiting example of a sampling range includes at least 2 mm and more preferably between about 2 and 20 mm.

Figure 7:
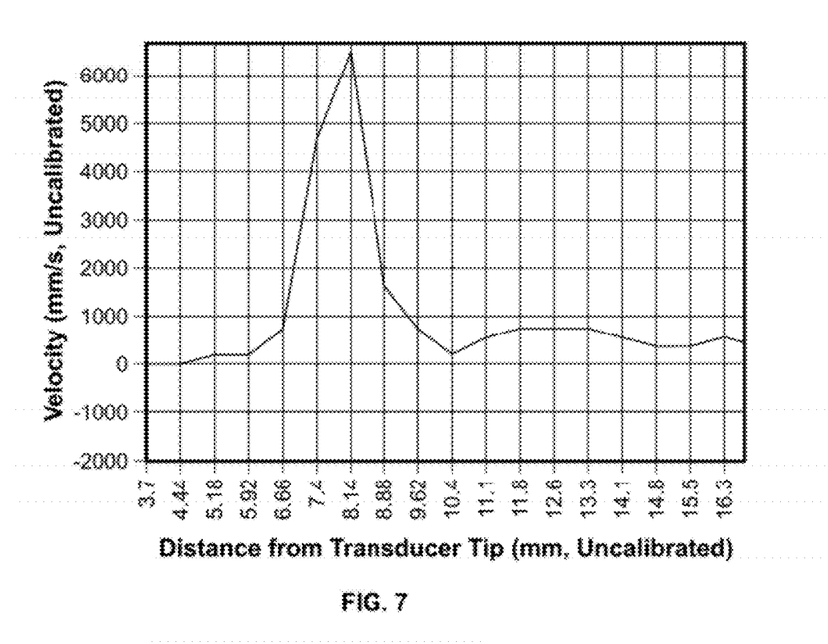
FIG. 7 is a plot of a velocity profile across a blood vessel as a function of distance from the Doppler probe in accordance with the present invention.

A temporal sampling rate is a rate to collect a plurality of instantaneous velocity profiles within a period of time. An illustration of a velocity profile is shown in FIG. 7, and corresponds to the set up shown in FIG. 6. The temporal sampling rate is preferably great enough to collect a sufficient number of instantaneous velocity profiles during each cardiac cycle, such that the time-averaged volume flow from these profiles is an accurate estimate of real volume flow. The temporal sampling rate is preferably at least twice (2×) that of the heart rate and is preferably as great as practicable so that the time variation of the flow velocity can be resolved within a heart beat and from heart beat to heart beat. Human heart rates are typically 60 to 120 beats per minute or 1-2 Hz. A non-limiting example sampling rate is between 5 and 20 samples/second.

The sampling period is the time to collect one sample velocity profile. The sampling period is the inverse of the sampling rate. Non-limiting examples of the sampling period is between 0.05 to 0.2 seconds/sample.

The sampling duration is the length of time during which sequential velocity profiles are captured and stored. It is preferably at least as long as a single heart beat and preferably is at least as long as several heartbeats.

The preferred time duration for sampling will be a function of the stability (i.e. repeatability) of the flow characteristics of the heart beat. For example, in the case of regular heart beat, a time duration of fewer than 10 consecutive heart beats is adequate. Nonlimiting examples of a time duration is between 2 and 20 seconds and more preferably between 6 and 10 seconds.

In an application, a large blood vessel is located by probing the bronchial airway walls with an ultrasound Doppler probe. A fluid velocity profile is continuously monitored using a Doppler processing unit. The fluid velocity profile may be shown on a display. An adjacent blood vessel is indicated by the observation of a time varying velocity waveform with a typical oscillating flow waveform, characteristic of pulsatile flow in a blood vessel. Confirmation is accomplished by observing the velocity curve with a central peak that decays spatially to approximately zero over a span of several millimeters. An example of such a velocity waveform with central peak is shown in FIG. 7. The velocity profile may consist wholly or in part of one or more negative flow regions. Negative flow, as defined here, corresponds to flow reversal with respect to positive flow. Flow reversal is typical of the temporal flow pattern of an artery within a living body, as is well known in the art. The designations "positive" and "negative" flow, as depicted herein, will be understood to depend upon the orientation of the ultrasound probe relative to the blood vessel under measurement.

Once the blood vessel to be monitored has been located, the instantaneous volume flow rate q(t) is determined. Instantaneous volume flow rate is determined by measuring and summing a plurality of flow rates (e.g., $Vol_N$ of FIG. 9a) across discrete area cross sections of the blood vessel. The approximate center of the blood vessel is computationally determined by examination of the instantaneous velocity profile data—the locations of peak velocities for several profiles are averaged to approximate the center of the blood vessel.

Figure 8:
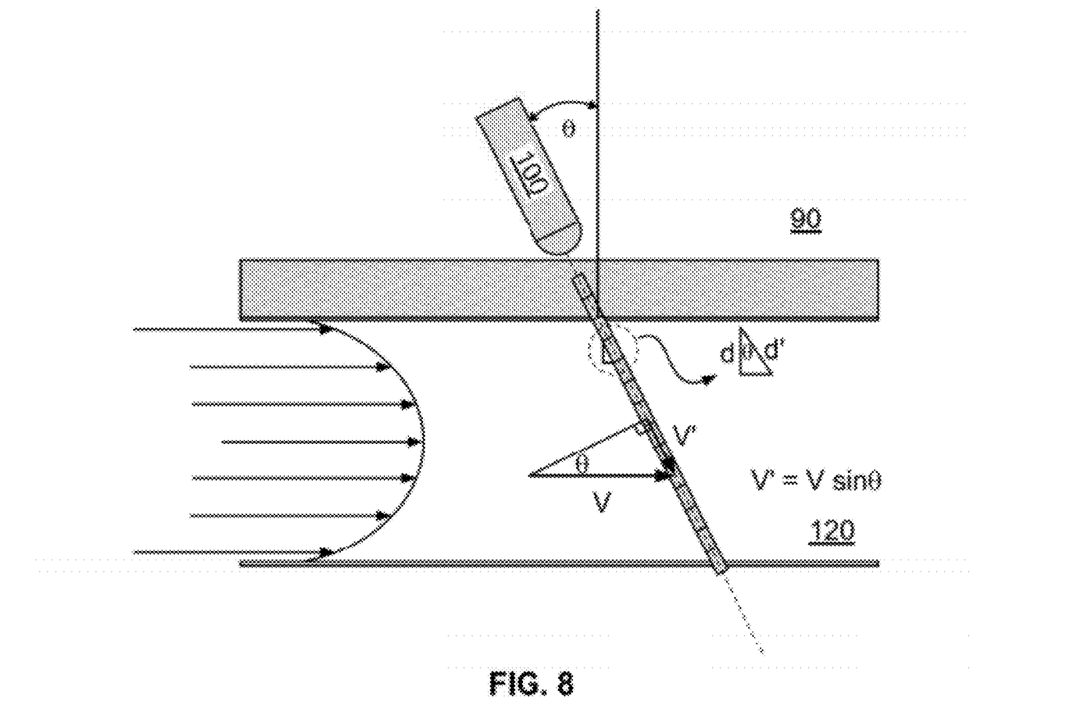
FIG. 8 is an illustration of an ultrasound Doppler probe within an airway and sending a beam through the blood vessel wherein the probe is positioned at an angle to the blood vessel.

Velocity at positions along the diameter of the vessel are detected using Doppler shift measurements, adjusted to account for the angle of the Doppler probe relative to the normal vector to the vessel. As illustrated in FIG. 8, the velocity of fluid traveling axially is equal to v'/sin(theta), where v' is the velocity measured along the angle theta. Theta may be determined as set forth above, or for example, as described in U.S. Pat. No. 4,103,679 (e.g., see column 4, lines 35-60), which is incorporated by reference in its entirety.

The calculation of instantaneous volume flow rate q(t) is iterative. To start the calculation, a first diameter is assumed—this may be equal to the length of one or two sample volume lengths (e.g., about 0.1 to 2 mm). This first diameter $d_0$ is centered over the approximate blood vessel axis (e.g., the spatial location where the velocity is highest) and is equal to the adjusted length of one or two pulsed wave ultrasound Doppler sampling volumes. Volumetric flow is calculated across this circular area defined by the following formula:

$$q_0(t)=u_0 *pi*d_0^2/4$$

where $q_0(t)$=instantaneous volume flow rate across a defined circular area, $u_0$=measured fluid velocity across defined circular cross section, and $d_0$=assumed diameter.

The instantaneous volume flow is then calculated by adding the volume flow calculations across successively larger annular areas, according to the following:

$$q_n(t)=q_0+\Sigma u_n *pi*(d_n^2-d_{n-1}^2)/4$$

Figure 9A:
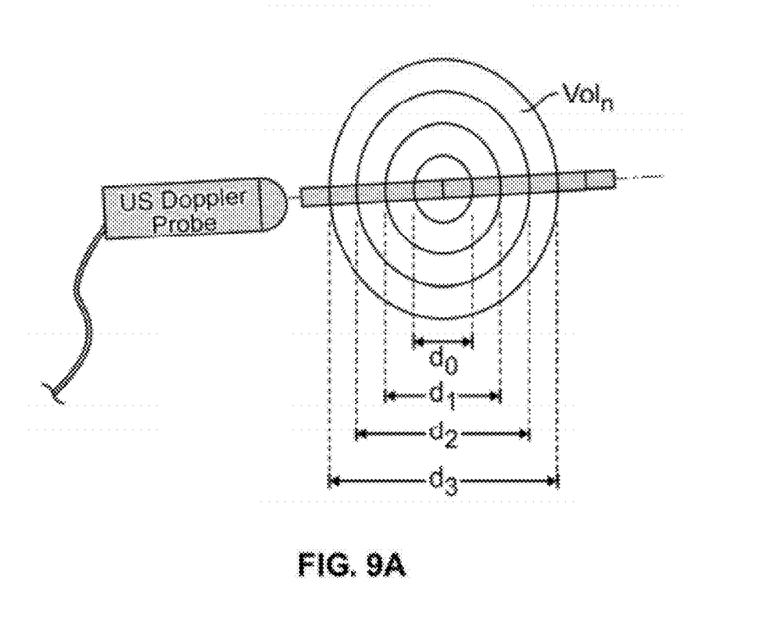
FIG. 9a is an illustration of a tissue region divided into a plurality of discrete sub-sections.
Figure 9B:
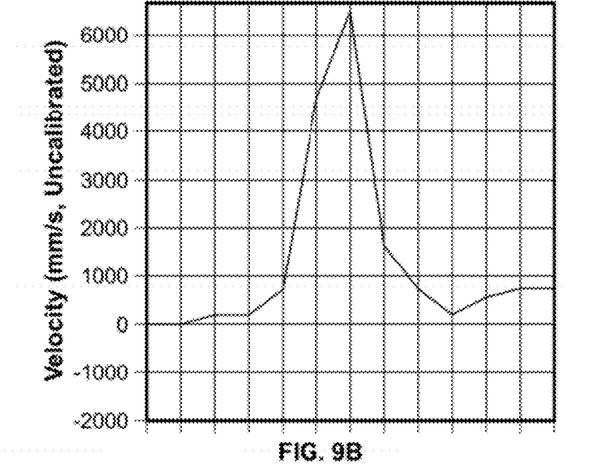

The velocity $u_n$ is the average of the velocities of the multiple sampling volumes that cross the annular area for each iteration n (see FIGS. 9a and 9b). This summation continues until subsequent calculations of $q_n(t)$ no longer increase or the rate of increase is below a pre-determined threshold, indicating that the Doppler sampling volumes are no longer within the vessel of interest. The value of $q_n(t)$ calculated in the last iteration is the instantaneous volume flowrate, q(t), calculated without the need to directly measure vessel diameter.

Volume flowrate calculated in this manner is accurate and free of errors associated with poor estimates of vessel diameter, or temporal variations in vessel diameter that are known to occur due to the compliant nature of arteries and veins. The number of iterations necessary in this step is determined by the mathematical convergence of q(t). Because the velocity profile within a blood vessel tends towards zero at the blood vessel walls, the contribution of the velocity rings to the calculation of volumetric flowrate is less for the peripheral rings and more for the central rings. Thus, as the calculation proceeds from the center to the periphery of the blood vessel, the value of the calculated volumetric flow rate will be seen to change more slowly as the inner edge of the blood vessel is approached. This provides a means of automatically identifying the diametric limits of the blood vessel and improves the accuracy of the calculation. Accuracy is further improved as the Doppler sampling volume is decreased.

Calculation of Time-Averaged Volume Flow Rate Q.

The time-averaged volume flow, calculated over several instantaneous velocity profiles within a heart beat and over the course of multiple heartbeats, yields an estimate of the net forward volume flow through the blood vessel. This time-averaged flow is described analytically as follows:
where $$Q = \frac{1}{\tau} \int_0^\tau q(t)\,dt$$

Q=time-averaged volume flow rate, and
τ=sampling period.

The analytical expression for volume flow rate Q, shown above, can be discretized for the estimation of volume flow from distinct digitized velocity profiles collected, for example, with a pulsed-wave ultrasound velocity probe. Velocity profiles can be measured at intervals of Δt, over a sampling period τ. The resulting estimate of average volume flow rate during the sampling period τ then becomes:

$$Q = \Delta t/\tau \sum_{n=0}^{\tau/\Delta t} q(t) \Delta t$$

For completeness the following is a combination of previous expressions and is the formula for volume flow estimation by the described method:

$$Q = \Delta t/\tau \sum_{n=0}^{\tau/\Delta t} \left( q_0 + \sum u_n * pi * (d_n^2 - d_{n-1}^2)/4 \right) \Delta t$$

The iterative calculation described above is preferably performed by automated computer processing of pulsed wave Doppler velocity data.

Figure 10:
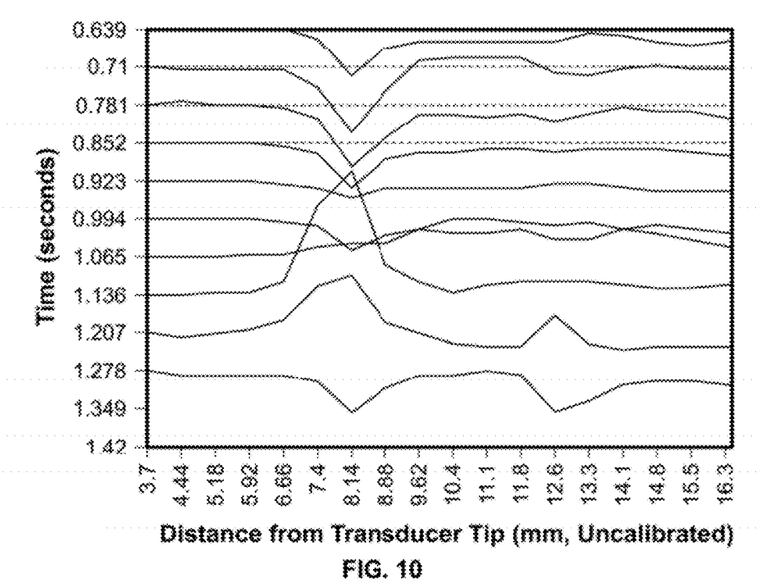
FIG. 10 is a plot of velocity profiles measured at different times.

FIG. 10 shows sequential velocity profiles captured during a sampling period in a canine blood vessel. The example data was obtained by collecting velocity profiles in a canine pulmonary blood vessel at a temporal sampling rate of approximately 7 Hz. The Doppler probe system used was a MetFlow UVP Duo with TX-8 transducer, Lausanne, Switzerland. In particular, a transbronchial catheter was advanced into an airway in the vicinity of the right branch of the pulmonary artery in the dog. This artery is typically 6-8 mm in diameter in a dog. Velocity data was then detected using the pulsed wave ultrasound probe.

It is noteworthy in FIG. 10 that the instantaneous velocity profiles vary within a heartbeat, as would be expected as the blood flow surges and then subsides and finally reverses within the different sub-stages of the heartbeat. The measurements are therefore preferably carried out over an extended time duration in order to obtain a time averaged flowrate representative of the net volume flowrate through the blood vessel. As discussed above, suitable time durations range from 6-10 seconds, or longer.

Figure 11:
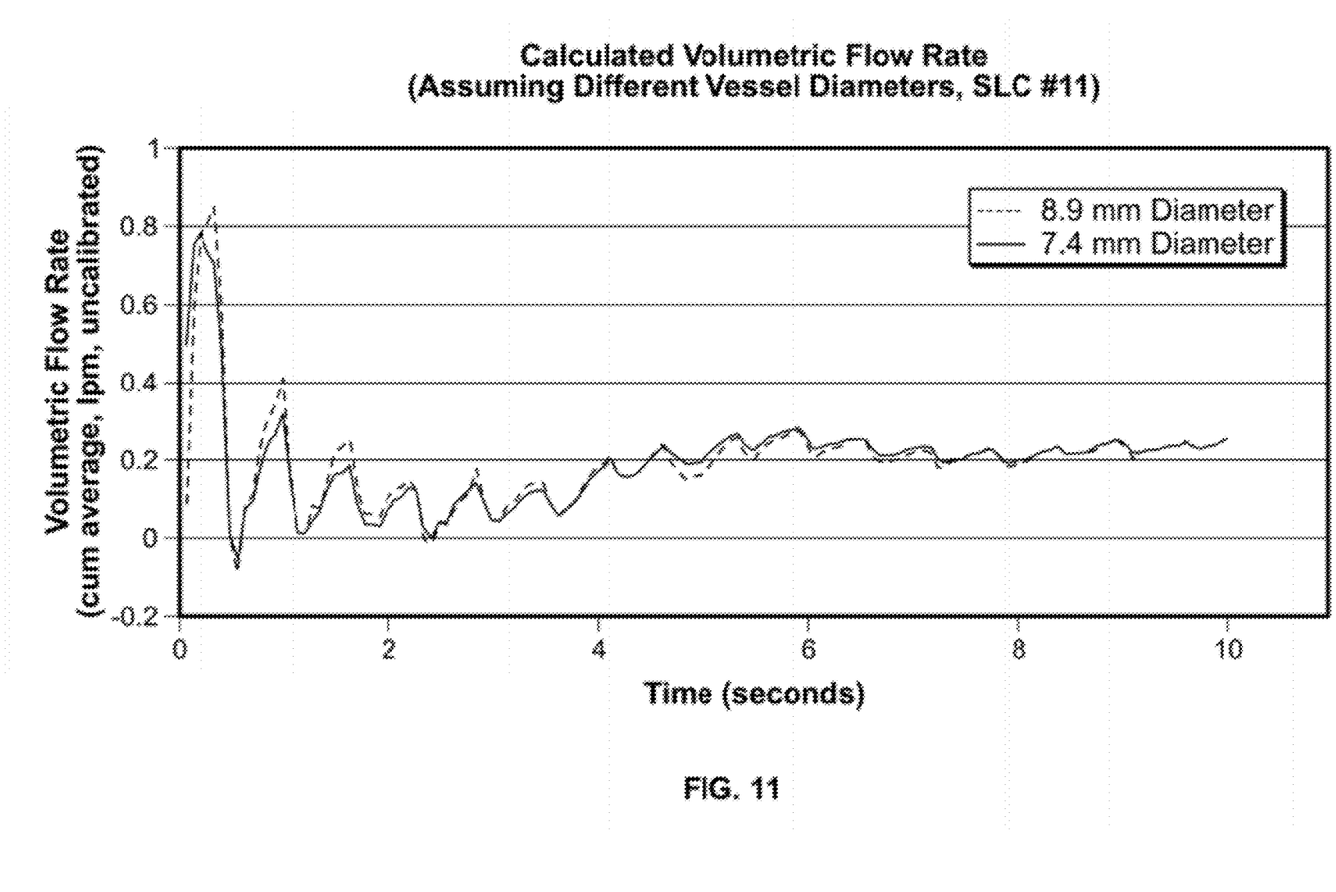
FIG. 11 is a plot of a flowrate calculated over a time duration in accordance with the present invention.

FIG. 11 shows two time-averaged volume flowrate lines. The lines represent time-averaged volume flowrates using different diameter thresholds as referred to in Section [0070]. The dashed line corresponds to an calculated maximum diameter of 8.9 mm, and the solid line corresponds to a calculated maximum diameter was 7.4 mm. Q(t) was calculated, as described above, namely, by adding component annular volume flowrates together. As shown, both lines converge to a nearly constant value after approximately 10 cardiac cycles (i.e. after approximately 6 seconds of data collection), indicating that a diameter of 8.9 mm does not subtend any additional flow and is therefore beyond the vessel wall; and that 7.4 mm is a correct representation of the vessel diameter. The data shown in FIG. 11 is uncalibrated, so the steady-state volume flow rate is not expected to be physiologic. However, calibration is a well known exercise to those having skill in the art.

FIG. 11, and in particular, the clear convergence of the two lines, suggests that so long as the sampling range spans the vessel and extends to the zero velocity regions along the edge of the vessel (or beyond), the present invention provides an estimate of the average flowrate regardless of the diameter of the vessel. Thus, so long as the conditions described above are met, and the iterative calculation for q(t) proceeds to a diameter greater than the vessel of interest, an accurate volume flowrate can be estimated.

Estimation of Cardiac Output.

Cardiac output may be estimated in accordance with the present invention. The right and left main pulmonary arteries are both positioned anatomically adjacent to the right and left main bronchi. Thus, by probing both of these arteries and summing the resulting blood volume flows, one will obtain an estimate of cardiac output. One can also obtain an estimate of cardiac output by probing one or the other of the right or left pulmonary arteries and doubling the blood volume flow from that artery. This latter method relies on the assumption that cardiac output blood volume flow is distributed equally to the right and left pulmonary arteries. After calibration of the system, it is expected that the invention would accurately estimate cardiac output in human subjects, with measurements in the physiological range of 1-10 liters per minute.

All patents, applications, and publications referenced above are hereby incorporated by reference in their entirety.

We claim:

1. A transbronchial medical system for measuring pulmonary circulation information of the pulmonary artery from the bronchi and without penetrating the pulmonary artery during a live procedure comprising:
   a transbronchial catheter comprising a flexible shaft and a distal section, said distal section comprising at least one ultrasonic transducer; and
   an ultrasound Doppler signal processing unit comprising:
   an output port for delivering outgoing electrical signals to said at least one ultrasonic transducer;

an input port for receiving incoming electrical signals from said at least one ultrasonic transducer;

a processor in communication with said output port and said input port and configured (a) to control the outgoing electrical signals delivered to said ultrasonic transducer; (b) to receive and analyze the incoming electrical signals for volumetric flowrate (Q) of the pulmonary artery using Doppler shifting and time of flight analysis; (c) to determine a precursor pressure signature of the fluid in the pulmonary artery using Doppler shifting; and (d) to identify a pulmonary arterial pressure (PAP) by comparing said precursor pressure signature to a database of pressure signatures determined prior to the live procedure wherein each of said predetermined pressure signatures has a corresponding mean pulmonary arterial pressure determined prior to the live procedure.

2. The system of claim 1 wherein said catheter comprises a longitudinal axis, and said at least one ultrasonic transducer comprises a first transducer having a first angle with respect to said axis of said catheter, and a second transducer having a second angle with respect to said axis of said catheter and said first angle and said second angle are different.

3. The system of claim 1, wherein said processor is further configured to calculate a TPR ratio where the TPR ratio is proportional to PAP and inversely proportional to Q.

4. The system of claim 2, wherein the outgoing and incoming ultrasonic signals are analyzed to determine velocity (V) and a diameter (D) of the pulmonary artery, and further determining Q based on V and D.

5. The system of claim 1 further comprising a bronchoscope through which said catheter is inserted.

6. The system of claim 4 further comprising a visual display adapted to display at least one of V and Q.

7. A method for determining pulmonary circulation information in a pulmonary artery of a patient during a live procedure without puncturing or opening the pulmonary artery, said method comprising:
providing an ultrasound Doppler catheter, said catheter comprising a distal section and at least one ultrasound transducer in said distal section;
advancing said distal section of said ultrasound Doppler catheter through a natural respiratory opening of the patient, and into an airway and to a location along an airway wall such that at least a portion of said distal section and said at least one ultrasound transducer is in proximity of the pulmonary artery;
sending and receiving ultrasonic waves to said pulmonary artery from said ultrasound transducer;
determining a measured pressure signature by analyzing the received ultrasonic waves; and
comparing the measured pressure signature to a database created prior to the live procedure, said database comprising one or more predetermined pressure signatures wherein each of said predetermined pressure signatures has an associated mean pulmonary arterial pressure measured prior to the live procedure.

8. The method of claim 7 wherein the one or more predetermined pressure signatures and associated mean arterial pressure are determined based on empirical data arising from directly measuring the mean pulmonary arterial pressure in a blood vessel of a participant subject with a sensor for a plurality of different precursor pressure signatures.

9. The method of claim 1 wherein the corresponding mean pulmonary arterial pressure was determined using a standard PAP measurement technique.

10. The method of claim 9 wherein the standard PAP technique is a right heart catheterization.

11. A transbronchial method for determining flowrate in a blood vessel in the thoracic cavity during a live procedure, said method comprising the steps of:
providing an ultrasound catheter, said catheter comprising a distal section and at least one ultrasound transducer in said distal section;
advancing said distal section of said catheter through a natural respiratory opening, and into an airway such that at least a portion of said distal section and said at least one ultrasound transducer is in proximity of the blood vessel;
sending ultrasound energy along a path across a tissue region, said tissue region including said blood vessel; and
analyzing reflected ultrasound energy to determine flowrate in said blood vessel wherein said analyzing comprises comparing a measured pressure signature to a database created prior to the live procedure, said database comprising one or more predetermined pressure signatures wherein each of said predetermined pressure signatures has an associated mean pulmonary arterial pressure measured prior to the live procedure.

12. The method of claim 11 wherein said analyzing comprises determining an instantaneous velocity profile across the tissue region, and computing an instantaneous flowrate in the blood vessel based on said instantaneous velocity profile.

13. The method of claim 12 wherein said instantaneous flowrate is calculated by, at least in part, computing a plurality of component flowrates corresponding to a plurality of discrete area cross sections across the tissue region.

14. The method of claim 13, wherein the discrete area is annulus.

15. The method of claim 14 further comprising identifying the center of the blood vessel prior to determining the step of computing a plurality of component flowrates.

16. The method of claim 11 further comprising determining a temporal flowrate by obtaining a plurality of instantaneous flowrates over a sampling duration and time-averaging said instantaneous flowrates over said sampling duration.

17. The method of claim 16 wherein said sampling duration is between 6 to 10 seconds.

18. The method of claim 14 wherein said analyzing step is based at least in part on a slant angle, said slant angle equal to an angle formed between the distal end of said catheter and a normal vector, said normal vector being normal to a central axis of the blood vessel.

19. The method of claim 11 wherein said ultrasound catheter operates using a sampling range sufficient to detect zero velocity in tissue proximal and distal to the blood vessel, and said sampling range being greater than the diameter of the blood vessel.

20. The method of claim 11 wherein said flowrate is determined without measuring an actual diameter of the blood vessel.

21. The method of claim 11, wherein the blood vessel is a pulmonary artery, and further comprising determining a mean PAP in the pulmonary artery, wherein said mean PAP is determined using ultrasonic waveform analysis and comprises comparing a measured pressure signature to a predetermined pressure signature.

22. The method of claim 21 further comprising calculating a TPR.

* * * * *